(12) United States Patent
Horne et al.

(10) Patent No.: US 10,661,022 B2
(45) Date of Patent: May 26, 2020

(54) SUBSTANCE DELIVERY DEVICE

(71) Applicant: Allergan Holdings France S.A.S., Courbevoie (FR)

(72) Inventors: Kenneth N. Horne, San Francisco, CA (US); Brian Domecus, San Francisco, CA (US)

(73) Assignee: Allergan, Inc., Irvine, CA (US)

( * ) Notice: Subject to any disclaimer, the term of this patent is extended or adjusted under 35 U.S.C. 154(b) by 59 days.

(21) Appl. No.: 15/950,862

(22) Filed: Apr. 11, 2018

(65) Prior Publication Data
US 2018/0228982 A1 Aug. 16, 2018

Related U.S. Application Data

(63) Continuation of application No. 14/604,498, filed on Jan. 23, 2015, now Pat. No. 9,968,745.
(Continued)

(51) Int. Cl.
*A61M 5/32* (2006.01)
*A61B 90/00* (2016.01)
(Continued)

(52) U.S. Cl.
CPC ........... *A61M 5/32* (2013.01); *A61B 17/3468* (2013.01); *A61B 90/03* (2016.02); *A61M 5/002* (2013.01);
(Continued)

(58) Field of Classification Search
CPC ................ A61M 5/2033; A61M 5/158; A61M 5/14248; A61M 5/20; A61M 5/30;
(Continued)

(56) References Cited

U.S. PATENT DOCUMENTS

| | | | |
|---|---|---|---|
| 842,631 A * | 1/1907 | Deperdussin | ..... A61M 37/0069 604/62 |
| 1,250,114 A | 12/1917 | Bigelow et al. | |

(Continued)

FOREIGN PATENT DOCUMENTS

| | | |
|---|---|---|
| EP | 2422832 A2 | 2/2012 |
| WO | 1992013579 A1 | 8/1992 |

(Continued)

OTHER PUBLICATIONS

Bleyer, Mark, SIS Facial Implant 510(k) Summary, Cook Biotech, Inc., May 19, 2005.

*Primary Examiner* — Manuel A Mendez
(74) *Attorney, Agent, or Firm* — Nathan S. Smith; Sujohn Das; Morgan, Lewis & Bockius LLP

(57) ABSTRACT

A substance delivery device that includes a hypodermic needle with a tube for receiving and containing a volume of a substance. The substance delivery device includes a rod, a portion of which is of a size and shape to fit within the tube of the hypodermic needle. The rod can be displaced into and within the tube to contact and apply a force to a volume of substance contained within the tube to cause, at least in part, the volume of substance to be discharged out of the tube. The substance delivery device includes a rod displacement mechanism that applies a force to the rod to cause the rod to be displaced into and within the tube. The substance delivery device also includes a needle retraction mechanism that is configured to apply a force to the hypodermic needle to cause the hypodermic needle to retract from within a patient.

10 Claims, 10 Drawing Sheets

Related U.S. Application Data

(60) Provisional application No. 61/932,016, filed on Jan. 27, 2014.

(51) Int. Cl.
  *A61B 17/34* (2006.01)
  *A61M 5/00* (2006.01)
  *A61F 2/00* (2006.01)
  *A61B 17/00* (2006.01)

(52) U.S. Cl.
  CPC . *A61M 5/3234* (2013.01); *A61B 2017/00792* (2013.01); *A61F 2/0059* (2013.01); *A61M 2005/004* (2013.01); *A61M 2005/005* (2013.01)

(58) Field of Classification Search
  CPC .. A61M 5/2448; A61M 5/19; A61M 5/31501; A61M 5/31596; A61M 5/326; A61M 5/2066; A61M 5/3287; A61M 5/1454; A61M 5/31526; A61M 5/3204; A61M 5/3202; A61B 17/0401; A61B 17/3468
  See application file for complete search history.

(56) References Cited

U.S. PATENT DOCUMENTS

| | | |
|---|---|---|
| 1,558,037 A | 10/1925 | Morton |
| 1,591,021 A | 7/1926 | Davis |
| 4,154,239 A | 5/1979 | Turley |
| 4,223,674 A * | 9/1980 | Fluent ............... A61M 37/0069 604/507 |
| 4,474,572 A | 10/1984 | McNaughton et al. |
| 4,518,384 A * | 5/1985 | Tarello ................... A61M 5/20 604/61 |
| 4,846,886 A | 7/1989 | Fey et al. |
| 4,957,744 A | 9/1990 | della Valle et al. |
| 5,211,644 A | 5/1993 | VanBeek et al. |
| 5,250,026 A | 10/1993 | Ehrlich et al. |
| 5,258,013 A | 11/1993 | Granger et al. |
| 5,478,327 A | 12/1995 | McGregor et al. |
| 5,824,335 A | 10/1998 | Dorigatti et al. |
| 6,053,899 A * | 4/2000 | Slanda ............... A61B 17/0483 604/500 |
| 6,214,030 B1 | 4/2001 | Matsutani et al. |
| 6,936,297 B2 | 8/2005 | Roby et al. |
| 7,041,088 B2 | 5/2006 | Nawrocki et al. |
| 7,504,386 B2 | 3/2009 | Pressato et al. |
| 7,559,952 B2 | 7/2009 | Pinchuk |
| 7,666,339 B2 | 2/2010 | Chaouk et al. |
| 7,722,582 B2 | 5/2010 | Lina et al. |
| 9,968,745 B2 * | 5/2018 | Horne ................... A61B 90/03 |
| 2001/0008937 A1 | 7/2001 | Callegaro et al. |
| 2002/0026039 A1 | 2/2002 | Bellini et al. |
| 2004/0192643 A1 | 9/2004 | Pressato et al. |
| 2005/0033362 A1 | 2/2005 | Grafton |
| 2006/0041320 A1 | 2/2006 | Matsuda |
| 2008/0167674 A1 | 7/2008 | Bodduluri et al. |
| 2009/0299328 A1 | 12/2009 | Mudd et al. |
| 2010/0256596 A1 | 10/2010 | Chomas |
| 2011/0263724 A1 * | 10/2011 | Gurtner ................. A61L 15/28 514/777 |
| 2013/0211374 A1 | 8/2013 | Heterington |
| 2014/0228971 A1 | 8/2014 | Kim |

FOREIGN PATENT DOCUMENTS

| | | |
|---|---|---|
| WO | 200100190 A2 | 1/2001 |
| WO | 2004022603 A1 | 3/2004 |
| WO | 2006-065837 | 6/2006 |
| WO | 2010028025 A1 | 3/2010 |
| WO | 2011109129 A1 | 9/2011 |
| WO | 2011109130 A1 | 9/2011 |
| WO | 2012054301 A1 | 4/2012 |
| WO | 2012054311 A1 | 4/2012 |
| WO | 2013082112 A1 | 6/2013 |
| WO | 2012174464 A3 | 5/2014 |

\* cited by examiner

SUBSTANCE DELIVERY DEVICE

This application is a continuation of U.S. patent application Ser. No. 14/604,498 filed Jan. 23, 2015 which claims priority to U.S. Provisional Patent Application No. 61/932,016, filed Jan. 27, 2014, each of which is incorporated herein by this specific reference.

BACKGROUND

As new substances have been developed for implanting into patients there exists a need for devices that are capable of quickly and easily delivering substances into patients. In particular, substances have been developed that are used to fill wrinkles, scars, and other marks on the skins of patients. These substances can be injected into patients close to the epidermis in order to properly function. Therefore, there exists a need for a device that is capable of delivering substances into a patient in a targeted manner to wrinkles, scars and marks all over a patient's body including the patients face. Generally, these substances are delivered into patients in an office setting in a quick procedure. Therefore, there exists a need for a device that is capable of delivering substances into a patient in a quick manner.

SUMMARY

The following embodiments and aspects thereof are described and illustrated in conjunction with systems, tools, and methods that are meant to be exemplary and illustrative, not necessarily limiting in scope.

In one embodiment, a substance delivery device is provided. The substance delivery device includes a hypodermic needle that includes a tube for receiving and containing a volume of a substance. The hypodermic needle includes an aperture on the distal end of the hypodermic needle that forms an opening to the tube within the hypodermic needle. The substance delivery device includes a rod. A portion of the rod is of a size and shape to fit within the tube of the hypodermic needle. The rod can be displaced into and within the tube to contact and apply a force to a volume of substance contained within the tube to cause, at least in part, the volume of substance to be discharged out of the tube. In one embodiment, the substance delivery device includes a rod displacement mechanism that applies a force to the rod to cause the rod to be displaced into and within the tube. Further in one embodiment, the substance delivery device also includes a needle retraction mechanism that is configured to apply a force to the hypodermic needle to cause the hypodermic needle to retract from within a patient.

These and other advantages will become apparent to those skilled in the relevant art upon a reading of the following descriptions and a study of the several examples of the drawings.

DETAILED DESCRIPTION

Device

Figure 1A:
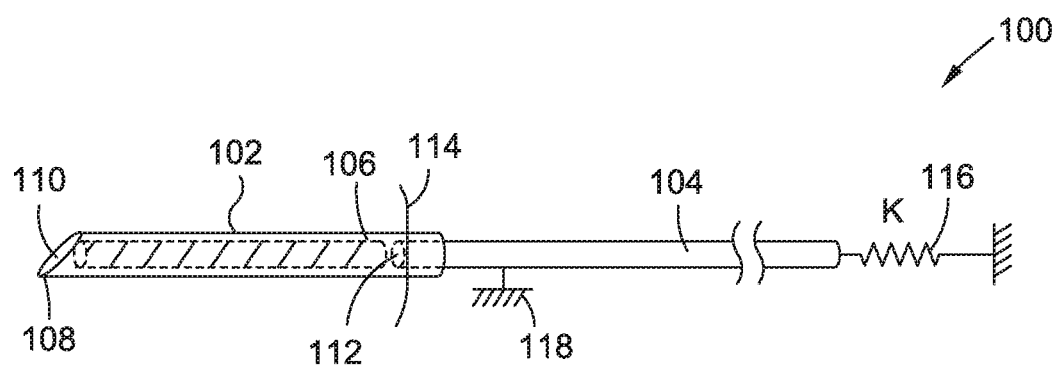
FIG. 1A depicts a cross-sectional view of an example of a substance delivery device in an example operational configuration.

FIG. 1A depicts a cross-sectional view of an example of a substance delivery device 100 in an example operational configuration. The example device 100 shown in FIG. 1A includes a hypodermic needle 102 and a rod 104. In the example operational configuration shown in FIG. 1A, the hypodermic needle 102 is inserted into a patient, underneath an outer surface of an epidermis 114 of a patient. Further in the example operational configuration shown in FIG. 1A, the hypodermic needle 102 can be inserted into a patient in a manner such that at least a portion of hypodermic needle 102 is in a specific desired region within a patient, such as the dermis, the subcutaneous tissue, or beneath the outer surface of the epidermis 114 of the patient.

The hypodermic needle 102 includes a tube 106 within the needle 102. The tube is a hollow region within the needle 102 that extends a length of the hypodermic needle 102. In one example, the tube 106 extends an entire length of the hypodermic needle 102. In another example, the tube 106 extends a portion of an entire length of the hypodermic needle 102.

The tube 106 functions to contain a substance. A substance contained by the tube 106 can be an applicable substance (e.g. a substance described in the compositions/substances section included herein) that is contained by the tube 106 and/or extruded through the tube 106.

The needle 102 includes a distal end 108. In one example, the distal end 108 of the needle 102 can be either blunt, beveled, or cone shaped. The distal end 108 of the needle 102 includes an aperture 110. The aperture 110 provides an opening to the tube 106, through which a substance contained within the tube 106 can pass out of the tube 106. In one embodiment, a substance contained within the tube 106 is passed out of the tube 106 as a result of extruding the substance out of the tube 106 by applying a force to the substance. In another embodiment, a substance contained within the tube 106 is passed out of the tube 106 by retracting the needle 102 from within a patient and applying a force to the substance as the needle 102 is retracted out of the patient. In an example of an operational configuration of the example device 100 shown in FIG. 1A, the hypodermic needle 102 can be positioned in a patient such that the aperture 110 is in a specific region in the patient, including the dermis region, the subcutaneous tissue region, or a region beneath the outer surface of the epidermis 114 of the patient. Further in another example of an operational configuration of the example device 100 shown in FIG. 1A, the hypodermic needle 102 is positioned in a patient such that the aperture 110 is at a position within the patient where it is desired to deposit a substance contained within the tube 106 into the patient.

The rod 104 functions to apply a force to a substance contained within the tube 106 of the hypodermic needle 102. In applying a force to a substance contained within the tube 106, the rod 104 is sized to fit within the tube 106. Specifically, the rod can move within the tube 106 to apply forces of various magnitudes to the substance contained within the tube 106. In one example, a diameter of the rod 104 is less than a diameter of the tube 106, such that the rod 104 can move within the tube 106 for at least a portion of a length of the tube 106.

The rod 104 includes a rod distal end 112, that contacts a portion of a volume of substance that is contained within the tube 106 as the rod 104 is displaced within the tube 106. In contacting a portion of a volume of substance contained within the tube 106, as the rod 104 is displaced within tube 106, the rod 104 applies a force to the volume of substance contained within the tube. In one example, the rod distal end 112 is of a shape or size or comprised of materials such that as the rod 104 applies a force to a substance contained within the tube 106, an amount of substance contained within the tube 106 that passes beyond the rod distal end 112 as the rod 104 is displaced within the tube 106 is minimized. For example, the rod distal end 112 can include a rubber plunger that remains in contact with walls of the tube as the rod 104 is displaced within the tube 106.

The example device 100 shown in FIG. 1A and the example substance delivery devices described throughout this paper can include a rod displacement mechanism, such as a spring-loaded mechanism 116. A rod displacement mechanism can be an applicable mechanism to cause the rod 104 to displace within the tube 106 away from a starting position towards a volume of substance contained within the tube 106. Specifically, a rod displacement mechanism can be an applicable mechanism to apply a force to the rod 104 to cause the rod to displace within the tube 106. In one embodiment, a rod displacement mechanism is used to cause the rod to displace and subsequently apply a force to a substance contained with the tube 106 to cause the substance to extrude out of the tube 106. In another embodiment, a rod displacement mechanism is used to cause the rod to displace within the tube 102 to a position where it applies a force to a substance contained within the tube as the needle 102 is retracted out of a patient, thereby discharging the substance into the patient.

The example device 100 shown in FIG. 1A and the example substance delivery devices described throughout this paper can include a rod retraction mechanism, such as the spring-loaded mechanism 116. A rod retraction mechanism can be an applicable mechanism to cause the rod 104 to retract towards a starting position after being displaced. In one embodiment a rod retraction mechanism causes the rod 104 to retract from within the tube 106 of the hypodermic needle 102 after the rod 104 is displaced into the tube 106. In one example a rod retraction mechanism is a spring-loaded bolt action mechanism that applies a force to the rod 104 to cause the rod 104 to retract towards a starting position. In another example, a rod retraction mechanism is a pneumatically-loaded bolt action mechanism that applies a force to the rod 104 to cause the rod 104 to retract towards a starting position. In one embodiment, a rod retraction mechanism is used to retract the rod 104 from within a patient after a volume of substance is extruded out of the tube 106. In another embodiment, a rod retraction mechanism is used to retract the rod 104 from within a patient as the rod 104 applies a force to a volume of substance contained within the tube 106, thereby discharging the substance into the patient.

The example device 100 shown in FIG. 1A and the example substance delivery devices described throughout this paper can include a rod locking mechanism, such as a switch 118. A rod locking mechanism can be a mechanism that engages the rod 104 and prevents the rod from displacing from within the tube 106. In one embodiment, a rod locking mechanism engages the rod 104 and prevents the rod 104 from displacing within the tube 106 after the rod 104 is displaced in the tube 106 to contact a portion of a volume of substance contained within the tube 106. Further in the one embodiment, a rod locking mechanism can lock the rod 104 in place as the needle 102 is retracted from within the patient, thereby causing the rod 104 to apply a force to a volume of substance contained within the tube 106 as the volume of substance is discharged into the patient.

Figure 1B:
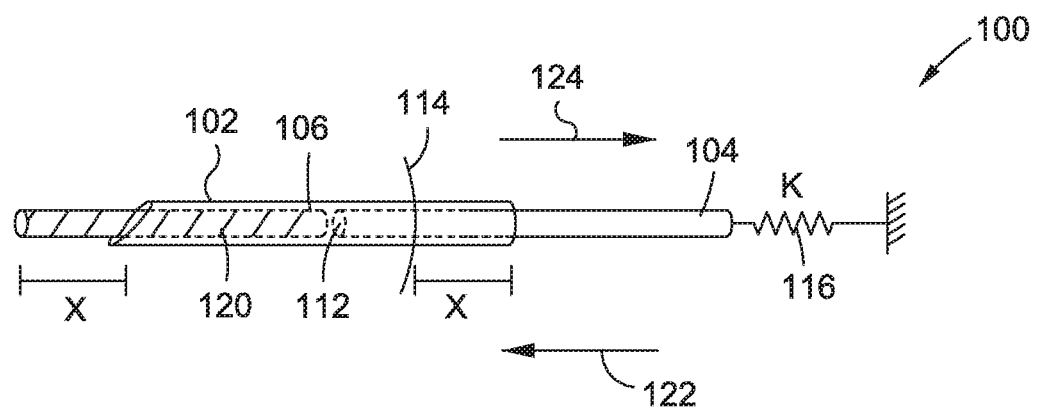
FIG. 1B depicts a cross-sectional view of an example of a substance delivery device in an example operational configuration.

FIG. 1B depicts a cross-sectional view of an example of a substance delivery device 100 in an example operational configuration. In the example operational configuration, the needle 102 is inserted into a patient, underneath an outer surface of an epidermis 114 of the patient. Further in the example operational configuration, the needle 102 is inserted underneath the outer surface of the epidermis 114 at a depth within the patient where it is desired to discharge a volume of substance 120 contained within the tube 106 of the needle 102.

In the example operational configuration shown in FIG. 1B, the rod 104 is displaced within the tube 106 along directional arrow 122. Further in the example operational configuration, the rod 104 is displaced a distance X within the tube 106. The rod 104 is displaced through a rod displacement mechanism, such as a spring-loaded mechanism 116. In one example, the spring-loaded mechanism includes a spring with a low k value to displace the rod 104. In various other examples, the rod displacement mechanism can be a twist-feed mechanism, a spring-loaded click mechanism, a sliding mechanism, a spring-loaded bolt action mechanism, or a pneumatically-loaded bolt action mechanism. As a result of displacing the rod 104 within the tube 106, a distal rod end 112 contacts the volume of substance 120 contained within the tube 106. Furthermore, displacing the rod 104 within the tube 106 along direction arrow 122, causes the rod 104 to apply a force to the volume of substance 120 contained within the tube 106. As the rod 104 is displaced a distance X within the tube 106, a portion of the volume of substance 120 contained within the tube 106 is extruded out of the needle 102 and into a patient. Further in the example operational configuration a portion of the volume of substance 120 corresponding to the distance X can be extruded out of the needle 102. For example a portion of the volume of substance with a length of X can be extruded out of the needle 102.

In various embodiments, the entire volume of substance 120 contained within the tube 106 is extruded out of the needle 102 into a patient. As a result, the volume of substance 120 does not extend out of an incision in a patient made by the needle 102, after the needle 102 is removed from within the patient, thereby leading to fast healing times. Further, if the volume of substance 120 is a dermal filler thread, in extruding the entire dermal filler thread into a patient, excess dermal filler thread does not need to be trimmed from an incision in a patient made by the needle 102, after the needle 102 is removed from within the patient.

Figure 1C:
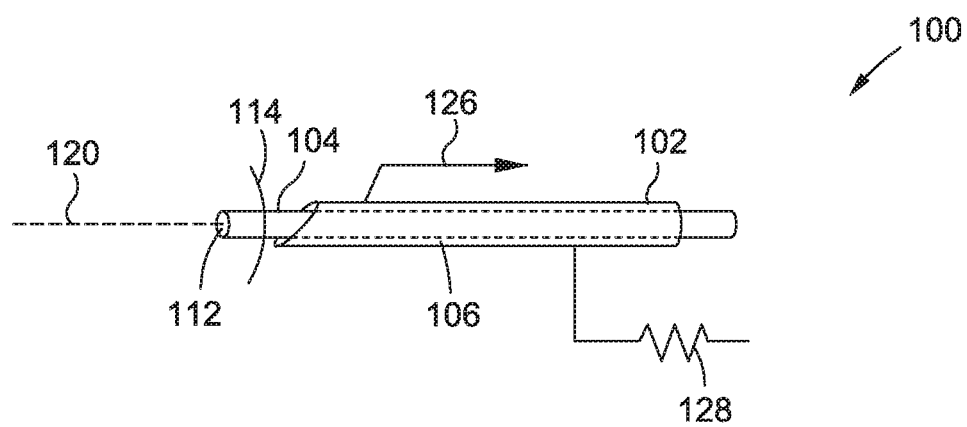
FIG. 1C depicts a cross-sectional view of an example of substance delivery device in another example operational configuration.

FIG. 1C depicts a cross-sectional view of an example of substance delivery device 100 in another example operational configuration. The example device 100 shown in FIG. 1C and the example substance delivery devices shown in this paper can include a needle retraction mechanism, such as a spring-loaded mechanism 128. A needle retraction mechanism can be an applicable mechanism to cause the needle 102 to retract out of a patient. In one example a needle retraction mechanism is a spring-loaded bolt action mechanism that applies a force to the needle 102 to cause the 102 to retract out of a patient. In another example, a needle retraction mechanism is a pneumatically-loaded bolt action mechanism that applies a force to the needle 102 to cause the needle 102 to retract out of a patient. In one embodiment, the needle retraction mechanism causes the entire needle 102 to retract from underneath the outer surface of the epidermis 114 and out of a patient.

In an example operational configuration shown in FIG. 1C, the needle 102 is inserted into a desired region in a patient, underneath the outer surface of the epidermis 114 of the patient. Further in the example operational configuration, the rod 104 is displaced within a tube 106 of the needle 102 such that rod distal end 112 contacts a volume of substance 120 contained within the tube 106.

Further in the example operational configuration, the rod 104 can be held in the position at which rod distal end 112 comes into contact with the volume of substance 120 contained within the tube 106 such that the rod distal end 112 remains in contact with the volume of substance 120 as the needle is retracted 102 from within a patient. The needle can be retracted from within a patient using an applicable needle retraction mechanism. The rod 104 can be held in place through either or both a rod displacement mechanism and a rod locking mechanism as the needle 102 is retracted from within a patient. Therefore, the rod 104 can apply a force to the volume of substance 120 as the needle 102 is retracted out of a patient to prevent the volume of substance 120 from moving in along direction 126 in which the needle 102 is retracted from within the patient. Further, as the rod 104 applies a force to the volume of substance 120 to prevent the volume of substance from moving in the direction 126 in which the needle 102 is retracted, the volume of substance 120 is discharged out of the tube 106 in the needle 102 and into the patient.

Figure 2:
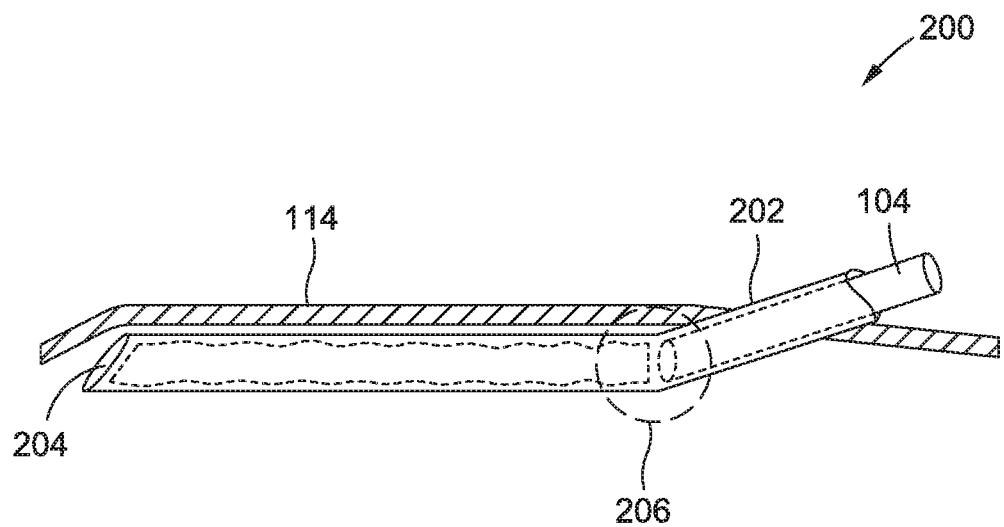
FIG. 2 depicts a cross-sectional view of an example of a substance delivery device with a curved needle.

FIG. 2 depicts a cross-sectional view of an example of a substance delivery device 200 with a curved needle. The example device 200 shown in FIG. 2 includes a curved hypodermic needle 202. The curved needle 202 curves in a curved region 206. Additionally, the curved needle 202 can include a curved tube 204 that curves within the curved region 206. In one example, the curved needle 202 is a Tuohy needle. By curving in the curved region 206, the curved needle 202 can be inserted into a patient and travel along a plane that is substantially parallel to a plane formed by an outer surface of an epidermis 114 of the patient. Additionally, by the curved needle 202 curving in the curved region 206, the example device 200 shown in FIG. 2 is capable of discharging a volume of substance 120 contained within the curved tube 204 into a patient along a plane that is substantially parallel to a plane formed by the outer surface of an epidermis 114 of the patient. Further, the example device shown in FIG. 2, can include a rod 104 configured to move within the curved tube 204 of the curved needle 202. For example, the rod 104 can be comprised of a flexible material, such as rubber, that allows the rod 104 to bend and pass through a curved portion of the curved tube 204 in the curved region 210 as the rod 104 is displaced within the curved tube 204 of the curved needle 202.

Figure 3:
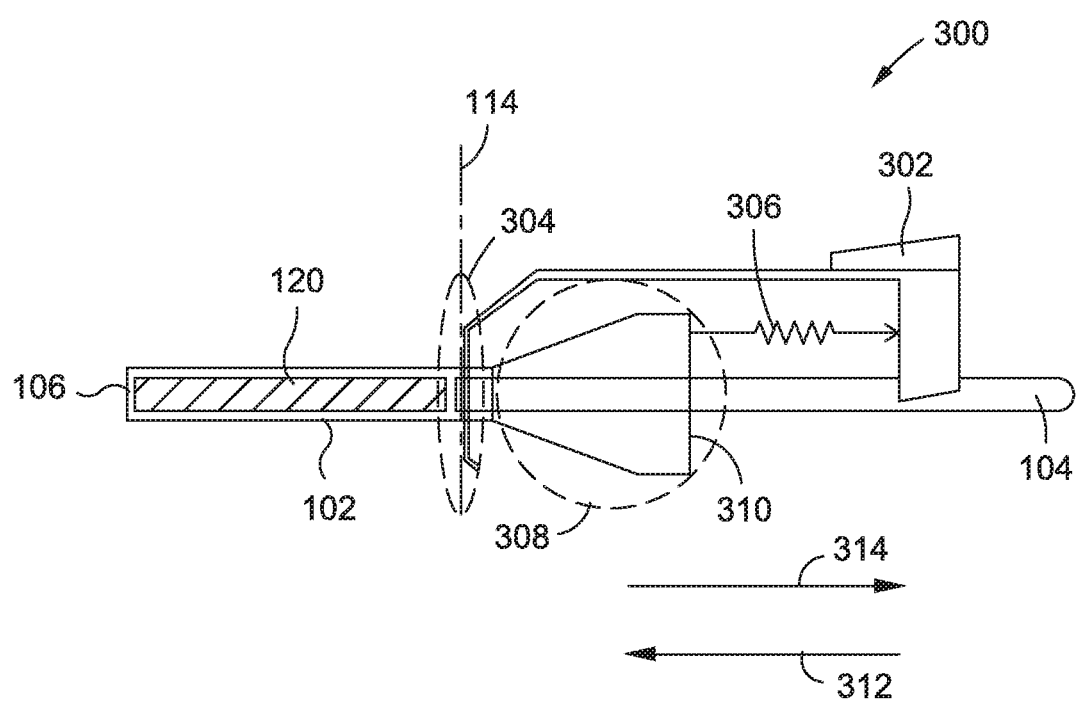
FIG. 3 depicts a cross-sectional view of an example of a needle substance delivery device with a needle retraction mechanism.

FIG. 3 depicts a cross-sectional view of an example of a needle substance delivery device 300 with a needle retraction mechanism. The example device 300 shown in FIG. 3A includes a needle 102 with a tube 106 for containing a volume of a substance 120. The example device shown in FIG. 3A also includes a rod 104 that is configured to fit and be displaced within the tube 106.

The example device 300 shown in FIG. 3 also includes a latching piece 302. The latching piece 302 can serve as a rod displacement mechanism to engage the rod 104 and cause displacement of the rod 104 within the tube 106. The latching piece 302 can engage the rod 104 through any applicable mechanism for engaging the rod 104 and allowing a force to be transferred and subsequently applied to the rod 104 to cause the rod to displace within the tube 106. For example the latching piece can engage the rod 104 through opposing grooves to transfer a force to the rod 104 and cause the rod 104 to be displaced within the tube 106. Additionally, the latching piece 302 can also serve as a rod locking mechanism. For example, the latching piece 302 can engage the rod 104 and transfer a force to the rod 104 to prevent the rod from being displaced within the tube 106. The latching piece 302 also includes an abutting region 304. In various embodiments, the abutting region 304 can include an opening or be of a shape to allow the needle 102 to thread through the abutting region 304.

The example device 300 shown in FIG. 3 includes a spring-loaded mechanism 306 that couples the latching piece 302 to the needle 102. Specifically, in the example device 300 shown in FIG. 3, the spring-loaded mechanism 306 is coupled to a flailed region 308 of the needle 102 that is located at the proximal end 310 of the needle 102. The spring-loaded mechanism 306 can serve as a needle retraction mechanism. Specifically, as the rod 104 is moved within the tube 106 along directional arrow 312, energy is stored in the spring-loaded mechanism 306. The energy stored in the spring-loaded mechanism 306 can then be used to generate and apply a force to the needle 102 to cause the needle 102 to retract out of the patient along directional arrow 314.

In the example operational configuration shown in FIG. 3, the abutting region 304 of the latching piece 302 comes into contact with an outer surface of the epidermis 114 of a patient. In coming into contact with the outer surface of the epidermis 114 of a patient, the abutting region 304 prevents the latching piece 302 from being inserted into the patient. Additionally, in coming into contact with an outer surface of the epidermis 114, the abutting region of the latching piece 302 provides leverage to either or both an operator of the example device 300 and the spring-loaded mechanism 306 in retracting the needle 102 from within the patient. In one embodiment, the abutting region 304 can be used to control the distance into a patient in which the needle 102 is injected. For example, the abutting region can be moved so that only the desired length of needle 102 extends out through the abutting region 304, wherein the abutting region prevents a length of needle that does not extend out through the abutting region 304 from being inserted into the patient.

In one embodiment, the volume of substance 120 contained within the tube 106 can be extruded into the patient by causing the rod 104 to displace down the entire length of the tube 106, thereby pushing the entire volume of substance 120 into the patient. Further in the one embodiment, after the volume of substance 120 is extruded into the patient, the needle 102 can be retracted from within the patient using the spring-loaded mechanism 306. In another embodiment, the needle 102 can be retracted from within the patient as the rod 104 is held in place by the latching piece 302, thereby causing at least a portion of the volume of substance 120 to discharge into the patient.

Figure 4A:
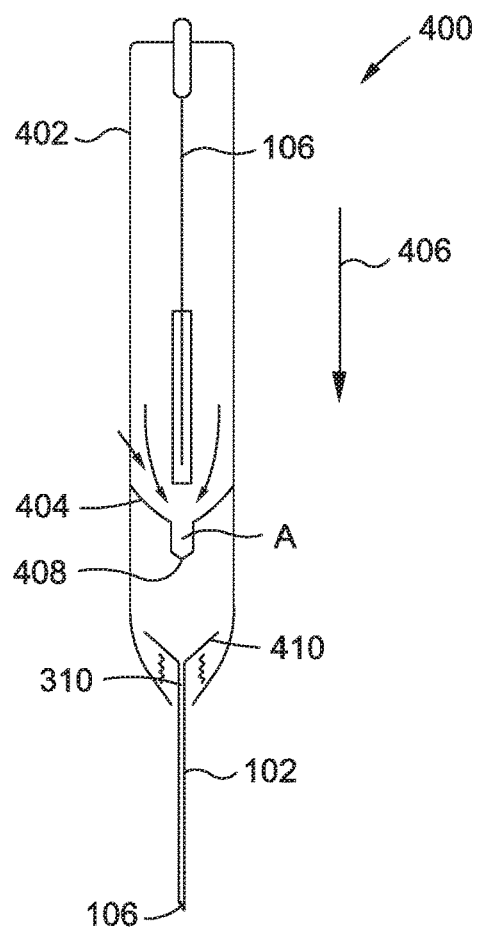
FIG. 4A depicts a cross-sectional view of an example of a substance delivery device that includes an internal taper guide.

FIG. 4A depicts a cross-sectional view of an example of a substance delivery device 400 that includes an internal taper guide. The example device 400 shown in FIG. 4A includes a hypodermic needle 102 and a rod 106. The example substance delivery device shown in FIG. 4A also includes a housing 402. The housing 402 is coupled to the needle 102 and the rod 106. The rod 106 is configured to move within the housing 402 and into a tube 106 within the needle 102.

In the example device 400 shown in FIG. 4A, the housing 402 includes an internal taper guide 404. The internal taper guide functions to control the displacement of the rod 106 within the housing 402 so that it is guided into a tube 106 within the needle 102 as the rod 106 is displaced within the housing 402 along directional arrow 406. In the example device 400 shown in FIG. 4A, the internal taper guide 404 can be one contiguous flange or a plurality of flanges that extend out from the inner surface of the housing. The one contiguous flange or plurality of flanges form a funnel aperture 408 through which the rod 104 is threaded through at it is displaced within the housing 402 along directional arrow 406. The funnel aperture 408 can be formed by positioned directly above or substantially directly above the tube within the needle 102 to cause the rod 106 to be positioned above and into the tube 106 within the needle 102.

The example device 400 shown in FIG. 4A also includes a needle taper guide 410. The needle taper guide 410 is formed as part of the needle 102 as flanges that extend out from the needle within the housing 402 at a proximal end 310 of the needle 102. The needle taper guide 410 can function to further guide a rod that is displaced within the housing 402 into a tube 106 within the needle 102.

Figure 4B:
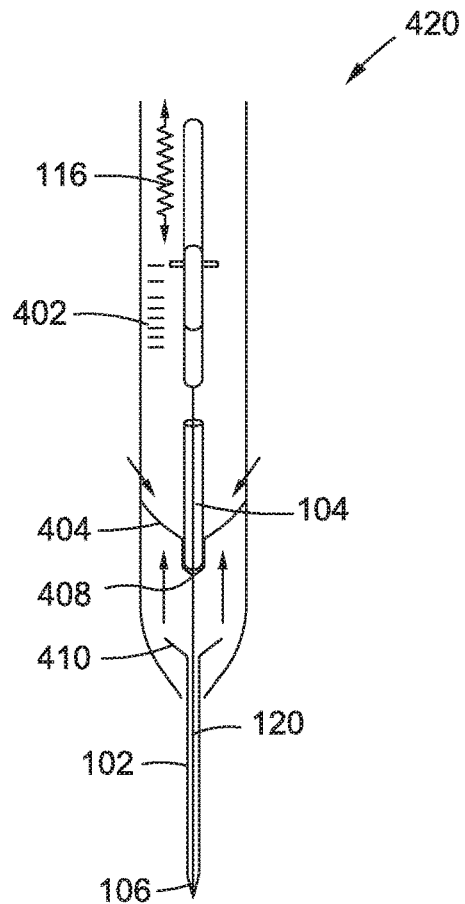
FIG. 4B depicts a cross-sectional view of an example of a substance delivery device that includes an internal taper guide configured to guide a volume of substance into a tube within a needle.

FIG. 4B depicts a cross-sectional view of an example of a substance delivery device 420 that includes an internal taper guide configured to guide a volume of substance into a tube within a needle. The example device 420 shown in FIG. 4B includes a hypodermic needle 102 with a tube 106. The needle 102 is coupled to a housing 402 that contains a rod 104 that is displaced within the housing 402. The rod 104 is configured to be displaced within the housing 402 and into and within the tube 106 of the needle 102. In the example device 420 shown in FIG. 4B, the housing 402 contains a volume of substance 120 that can be displaced within the housing 402 and into the tube 106 within the needle 102 and subsequently discharged into a patient.

In the example device 420 shown in FIG. 4B, the rod 104 is configured be displaced to contact the volume of substance 120 and apply a force to the volume of substance 120. The force applied to the volume of substance 120 by the rod 104 causes the volume of substance 120 to move within the housing 402 into the tube 106 within the needle 102. The example device 420 shown in FIG. 4B includes a spring-loaded mechanism 116 that serves as a rod displacement mechanism to cause the rod 104 to displace and apply a force to the volume of substance 120. In various embodiments, an applicable rod displacement mechanism can be used to cause the rod 104 to displace and subsequently apply a force to the volume of substance 120.

The example device 420 shown in FIG. 4B includes an internal taper guide 404. The internal taper guide 404 forms a funnel aperture 408 through which the rod 104 is thread through as the rod 104 is displaced within the housing 402. Additionally, the internal taper guide 404 forms a funnel aperture 408 through which the rod 104 is thread through as the rod 104 applies a force to the volume of substance 120. The internal taper guide 104 functions to guide the rod 104 as the rod applies a force to the volume of substance 120 contained within the tube, such that the volume of substance 120 is displaced towards the tube 106 within the needle 102. In various embodiments, the internal taper guide 104 can function to guide the volume of substance 120 contained within the housing 402 towards the tube 106 within the needle 102 as the volume of substance 120 is displaced within the housing towards the tube 106.

The example device 420 shown in FIG. 4B also includes a needle taper guide 410. The needle taper guide functions to guide either or both the rod 104 and a volume of substance 120 contained within the housing into the tube 106.

Figure 5:
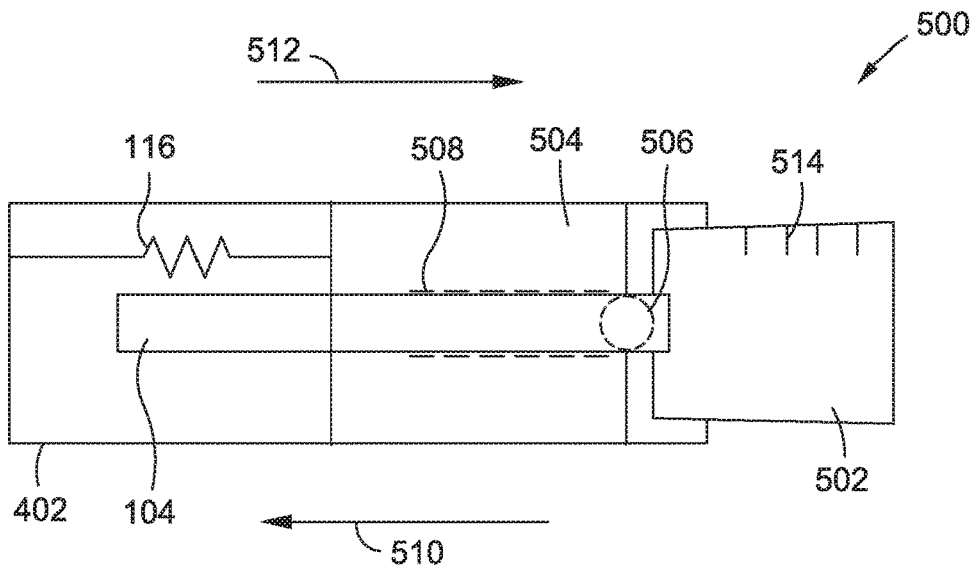
FIG. 5 depicts a cross-sectional view of an example of a substance delivery device with a rod displacement mechanism that is a twist-feed mechanism.

FIG. 5 depicts a cross-sectional view of an example of a substance delivery device 500 with a rod displacement mechanism that is a twist-feed mechanism. The example device 500 shown in FIG. 5 includes a housing 402 that contains a rod 104 that is configured to move within the housing 402. The rod 104 is coupled to a to a twist displacer piece 502 that serves, in part, as a twist feed mechanism in causing the rod 104 to displace within the housing 402. In the example device 500 shown in FIG. 5, the twist displacer piece 502 is rigidly secured to the rod 104 so that a rotational force that is applied to the twist displacer piece 502 is translated to the rod 104. Similarly, in being rigidly secured to the rod 104, a linear force that is applied to the rod is translated to the twist displacer piece 502.

In the example device 500 shown in FIG. 5, the housing 402 houses a threaded engagement piece 504. In various embodiments, the threaded engagement piece 504 is secured within the housing 402 to not move within the housing. The thread engagement piece 504 includes a threaded opening 506 through which the rod 104 can extend. The thread engagement piece 504 is coupled to the rod 104 through threads 508 in the threaded opening 506. Specifically, in the example device 500. The threads 508 functions to translate rotation force applied to the twist displacer piece 502 into linear force, thereby causing the rod 104 to displace along directional arrows 510 and 512 as a rotational force is applied to the twist displacer piece 502.

Additionally, in the example device 500 shown in FIG. 5, as the rod 104 is rigidly secured to the twist displacer piece 502, the linear displacement of the rod 104 within the housing 402 causes the twist displacer piece 502 to linearly displace as the rod 104 is linearly displaced. Therefore, when a rotational force is applied to the twist displacer piece 502 to cause the rod 104 to linearly displace through the threads 508 coupling the rod 104 to the thread engagement piece 504, the twist displacer piece 502 linearly displaces. The twist displacer piece 502 includes graduations 514. The graduations 514 can include indicia that indicate an amount that the twist displacer piece 502 has been linearly displaced into the housing 402. As the rod 104 is rigidly secured to the twist displacer piece 502, the graduations 514 can be used to indicate the amount that the rod 104 has been displaced within the housing 402. In various embodiments, the graduations 514 can be used to indicate an amount of a volume of substance that has been displaced into a tube within a needle.

The example device 500 shown in FIG. 5 includes a spring-loaded mechanism 116. In the example device 500 shown in FIG. 5, the spring-loaded mechanism 116 couples the thread engagement piece 504 to a needle. In various embodiments, the spring-loaded mechanism 116 can function to cause a needle to retract into the housing 402.

Figure 6A:
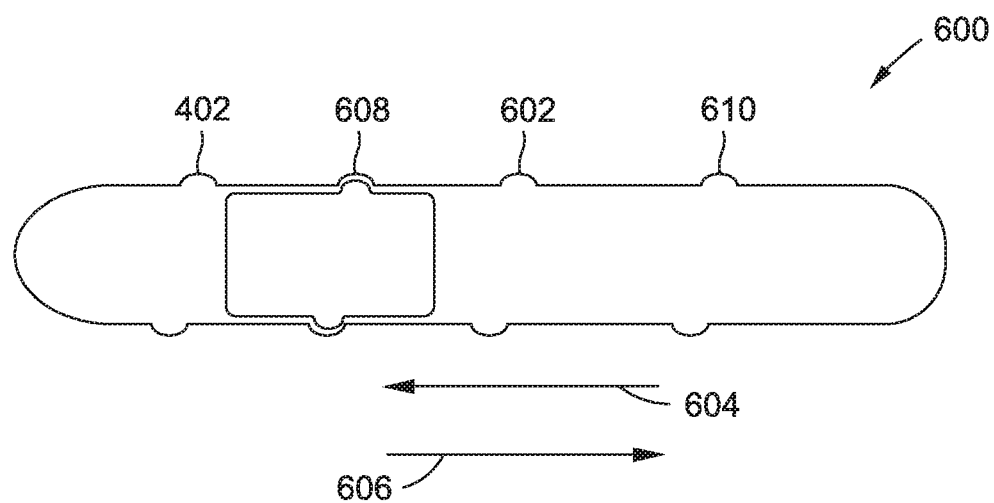
FIG. 6A depicts a top view of an example of a substance delivery device with a rod displacement mechanism that is a manual sliding mechanism.

FIG. 6A depicts a top view of an example of a substance delivery device 600 with a rod displacement mechanism that is a manual sliding mechanism. The example substance delivery device shown in FIG. 6A includes a housing 402. The housing 402 can contain a rod that is displaced within the housing 402 to apply a force to a volume of substance contained within a hypodermic needle.

The example device 600 shown in FIG. 6A also includes a sliding bar 602 that forms part of a manual sliding mechanism. The sliding bar 602 is configured to move along an outer surface of the housing 402 in directions indicated by directional arrows 604 and 606. The sliding bar 602 is coupled to a rod that is contained within the housing 402. As a result of the coupling between the sliding bar 602 and a rod contained within the housing 402, moving the sliding bar 602 causes the rod to displace. Therefore, the sliding bar 602 serves part of a manual sliding mechanism that is a rod displacement mechanism. In one embodiment, a rod is coupled to the sliding bar 602 such that the rod is displaced in the same direction as the sliding bar 602 is displaced.

The example substance delivery device shown in FIG. 6A can include grooves 608 that engage portions of the sliding bar 602 to prevent the sliding bar 602 from being displaced. As the sliding bar 602 is coupled to a rod contained within the housing 402, the groves 608, in preventing the sliding bar 602 from being displaced 602 can prevent the rod from being displaced, and thereby serve as a rod stopping mechanism.

The housing 402 of the example device 600 shown in FIG. 6A includes graduated indicia 610 indicating graduated measurements. The graduated measurements can represent the amount that the sliding bar 602 has been moved. As follows, since the sliding bar 602 is coupled to a rod within the housing, the graduated measurements can be the represent the amount that the rod has been displaced. In one example, an operator can use the graduated measurements to determine the amount of a volume of a substance that has been discharged or will be discharged into a patient.

Figure 6B:
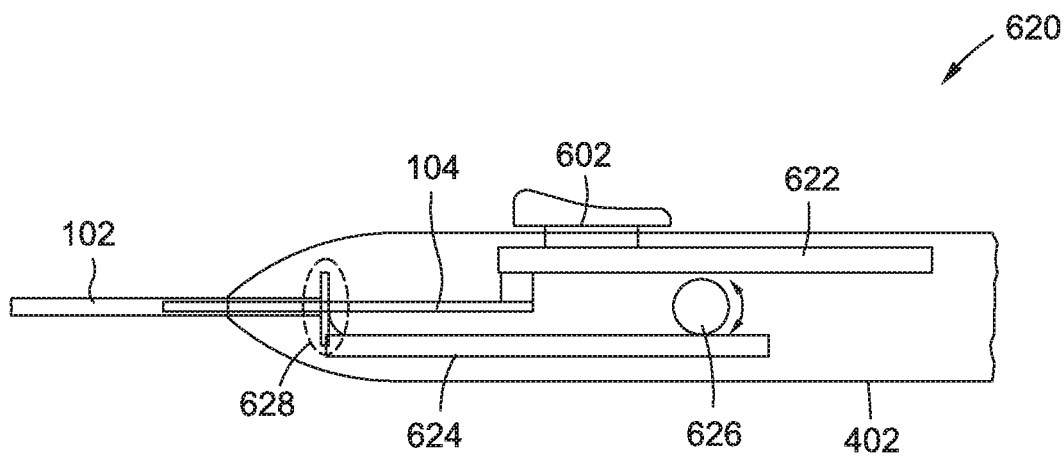
FIG. 6B depicts a cross-sectional view of an example of a substance delivery device with a rod displacement mechanism that is a sliding mechanism.

FIG. 6B depicts a cross-sectional view an example of a substance delivery device 620 with a rod displacement mechanism that is a sliding mechanism. The example device 620 shown in FIG. 6B includes a housing 402 and a sliding bar 602. The sliding bar 602 extends into the housing 402 where it is guided by a sliding bar guide 622. The sliding bar guide 622 functions to limit displacement of the sliding bar 602 to lateral displacement of the sliding bar 602.

In the example device 620 shown in FIG. 6B, the sliding bar 602 is coupled to a rod 104. The rod 104 is configured to move within the housing 402 into a tube within a needle 102 coupled to the housing 402.

The example device 620 shown in FIG. 6B includes a rod guide 624 and a gear 626. The sliding bar guide 622 and corresponding rod 104 is rotationally coupled to the rod guide 624 through the gear 626. Specifically, in being rotationally coupled, as the sliding bar 644 and the sliding bar guide 622 is moved, the gear 626 rotates along the rod guide 624, thereby ensuring that the sliding bar 602, the sliding bar guide 622 and the rod 104 is displaced in a roughly linear fashion. In the example device 620 shown in FIG. 6B, the rod guide 614 includes a taper guide 628. The taper guide 628 functions to guide the rod 104 into a tube within the needle 102.

Figure 7:
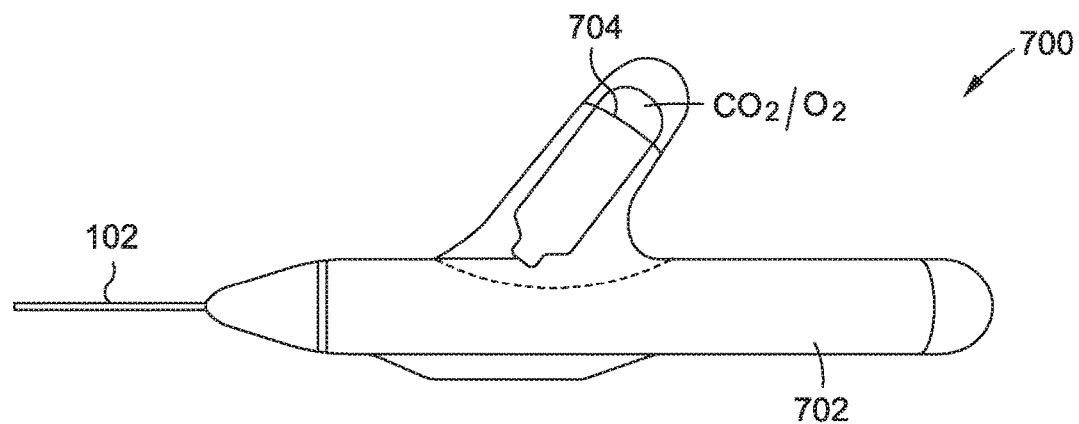
FIG. 7 depicts a cross-sectional view of an example of a substance delivery device with a rod displacement mechanism that is a pneumatically-loaded bolt action mechanism.

FIG. 7 depicts a cross-sectional view of an example of a substance delivery device 700 with a rod displacement mechanism that is a pneumatically-loaded bolt action mechanism. The example device 700 shown in FIG. 7 includes a housing 702 that is coupled to a hypodermic needle 102.

The example device 700 shown in FIG. 7 includes a pneumatically-loaded bolt action mechanism that serves as a rod displacement mechanism. The pneumatically-loaded bolt action mechanism can be any pneumatic based mechanism for applying a force to a rod contained within the housing 702 to cause the rod to move. The example device 700 shown in FIG. 7 includes a pressurized gas or liquid reservoir 704 that can pneumatically load the pneumatically-loaded bolt action mechanism. For example, the pressurized gas or liquid reservoir 706 can be a $CO_2$ canister. In the example device 700 shown in FIG. 7, the housing 702 is configured to house or receive the pressurized gas or liquid reservoir 704.

The example substance delivery device shown in FIG. 7 can also include a pneumatically-loaded bolt action mechanism that serves as a rod retraction mechanism. The pneumatically-loaded bolt action mechanism can be an applicable pneumatic based mechanism for applying a force to a rod contained within the housing 702 to cause the rod to retract towards a starting position. The pneumatically-loaded bolt action mechanism can be pneumatically loaded using the pressurized gas or liquid reservoir 704.

Figure 8:
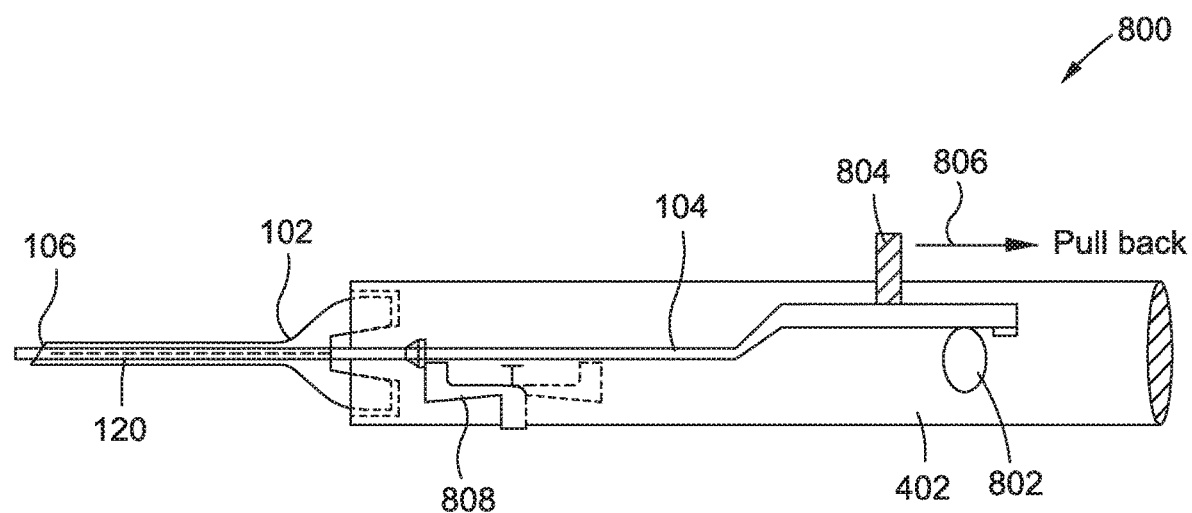
FIG. 8 depicts a cross-sectional view of an example of a substance delivery device with a rod displacement mechanism that is a spring-loaded bolt action mechanism.

FIG. 8 depicts a cross-sectional view of an example of a substance delivery device 800 with a rod displacement mechanism that is a spring-loaded bolt action mechanism. The example substance delivery device shown in FIG. 8 includes a housing 402 that is coupled to a hypodermic needle 102. The hypodermic needle 102 includes a tube 106 that can contain a volume of substance 120 to be discharged into a patient. The housing 402 contains a rod 104 that can be displaced into and within a tube 106 of the hypodermic needle 102.

In the example device 800 shown in FIG. 8, the rod 104 is operationally coupled to a spring-loaded gear 802. The rod 104 is also coupled to a cocking piece 804 that extends out of the housing 402. The spring-loaded gear 802 and the cocking piece 804 can function to form at least part of a spring loaded-bolt action mechanism. An operator of the example substance delivery device can engage the cocking piece to cause the rod 104 to displace along direction arrow 806 to a cocked position. In one example, a cocked position can vary based on the amount of a volume of substance that an operator wishes to discharge into a patient. In being operationally coupled to the spring-loaded gear 802, the displacement of the rod 104 along direction arrow 806 causes the spring-loaded gear 802 to store rotate. As the spring-loaded gear 802 rotates it stores energy that can be used to apply a force to the rod 104 to cause the rod 104 to linearly displace.

The example device 800 shown in FIG. 8 includes a trigger lock 808 that functions as a rod locking mechanism to prevent the rod 808 from being displaced into a tube 106 within the hypodermic needle 102. Specifically, the trigger lock 808 prevents the rod 104 from being displaced as a force is applied to the rod by the spring-loaded gear 802. The trigger lock 808 is configured to allow the rod 104 to move freely along direction arrow 806 as an operator of the device 800 moves the rod 104 into a cocked position. In one example, the trigger lock 808 is spring activated, whereby pushing a button causes the trigger lock to disengage. The trigger lock 814 can be disengaged such that it no longer keeps the rod 806 locked from displacing into a tube 106 within the needle 102 after the rod 104 is pushed to a cocked position.

Figure 9A:
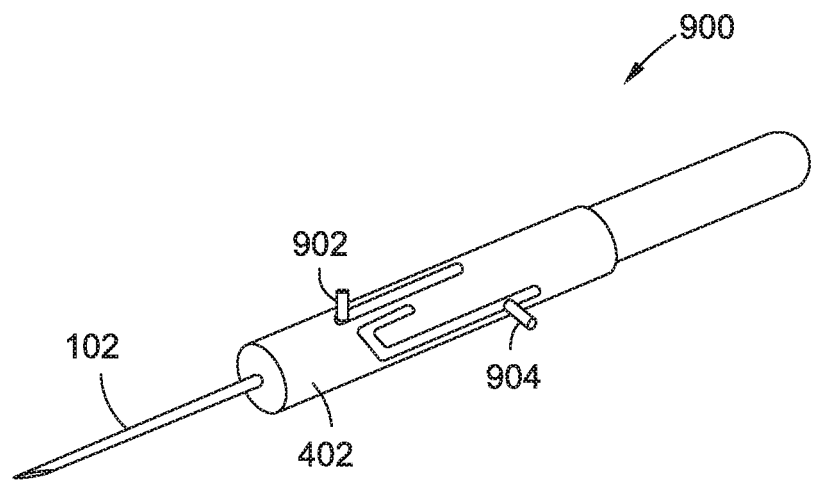
FIG. 9A depicts a perspective view of an example of a substance delivery device with a rod displacement mechanism and a needle retraction mechanism.

FIG. 9A depicts a perspective view of an example of a substance delivery device 900 with a rod displacement mechanism and a needle retraction mechanism. The example device 900 shown in FIG. 9 includes a housing 402 that is coupled to a hypodermic needle 102. The housing contains a rod that can be displaced into and within a tube in the hypodermic needle 904. The example substance delivery device includes a needle cocking piece 902 that forms part of a needle retraction mechanism. In one example the needle retraction mechanism is a spring-loaded bolt action mechanism. The needle cocking piece 902 is coupled to the hypodermic needle 102 such that the as the needle coking piece 902 moves so does the needle 102. As a result displacing the needle cocking piece 902 causes the needle 102 to move out from or retract into the housing 402. The needle retraction mechanism can function as a needle locking mechanism when the needle cocking piece 902 is at a cocked position corresponding to the needle 102 extending from the housing 402. Specifically, in functioning as a needle locking mechanism, the needle retraction mechanism can hold the needle 102 in place while it is extended form the housing 402.

The example device 900 shown in FIG. 9A also includes a cocking piece 904 that forms part of a rod displacement mechanism. The cocking piece 904 is coupled to a rod within the housing and causes the rod to displace when a user moves the cocking piece 904. The rod displacement mechanism formed in part by the cocking piece 904 can be used to load a volume of substance contained within the housing 402 into a tube within the needle 102. Additionally, the rod displacement mechanism formed in part by the cocking piece 904 can be used to discharge a volume of substance from a tube in the needle 102 into a patient.

Figure 9B:
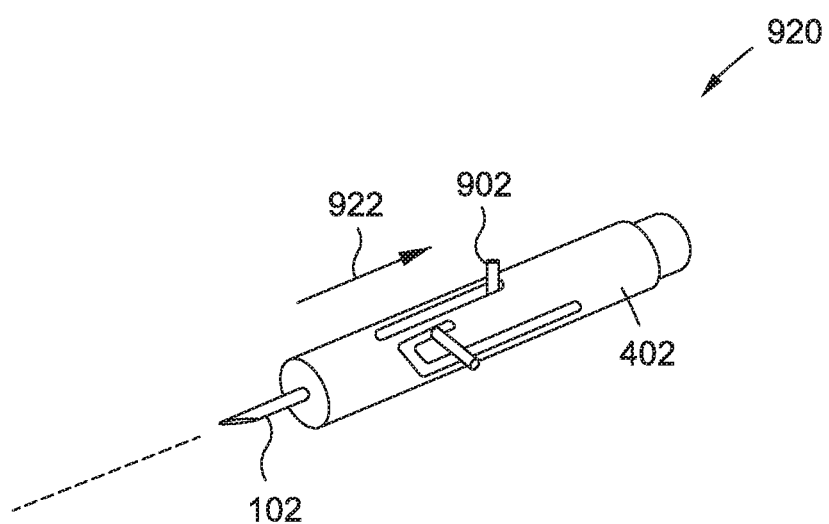
FIG. 9B depicts a perspective view of an example of a substance delivery device with a rod displacement mechanism and a needle retraction mechanism after a needle is retracted from within a patient.

FIG. 9B depicts a perspective view of an example of a substance delivery device 920 with a rod displacement mechanism and a needle retraction mechanism after a needle is retracted from within a patient. The example device 920 shown in FIG. 9B includes a needle cocking piece 902 that forms part of a needle retraction mechanism. In one example the needle retraction mechanism is a spring-loaded bolt action mechanism. The needle cocking piece 902 is coupled to a hypodermic needle 102. Upon being activated, the needle retraction mechanism causes the needle 102 to retract into the housing 402. Additionally, upon activating the needle retraction mechanism, the needle cocking piece 902 moves along direction arrow 922 as the needle retracts into the housing 402.

Figure 10:
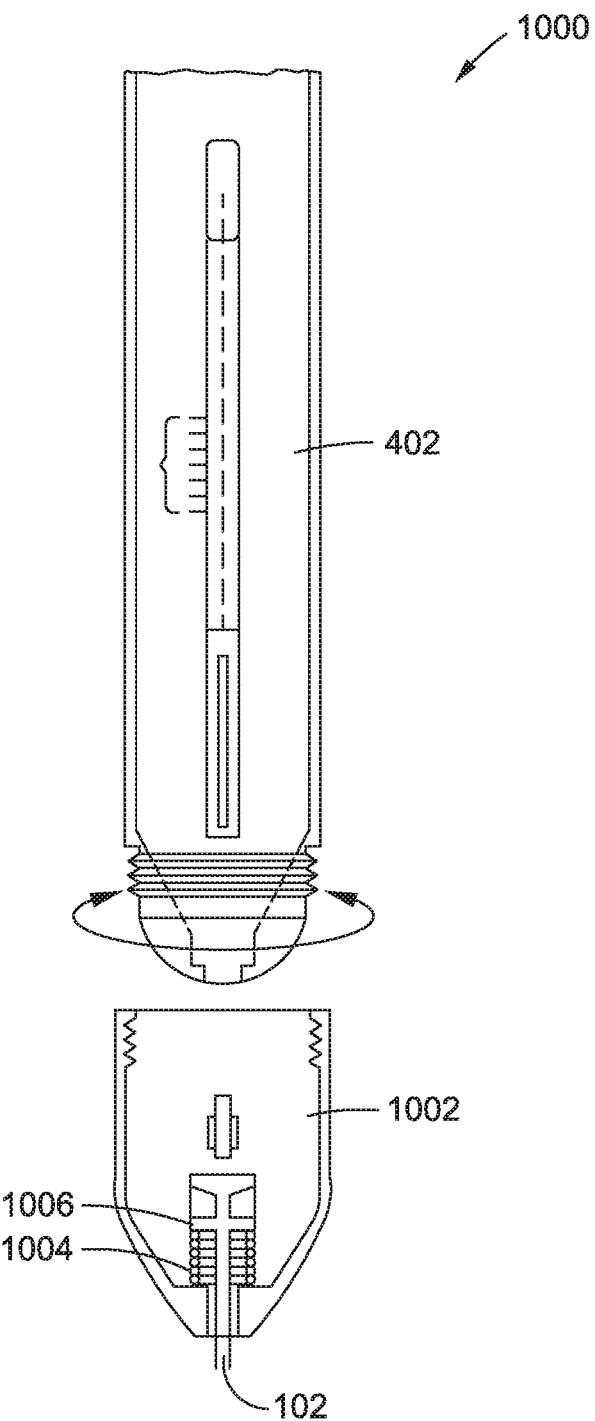
FIG. 10 depicts a cross-sectional view of an example of a substance delivery device with a needle retraction mechanism.

FIG. 10 depicts a cross-sectional view of an example of a substance delivery device 1000 with a needle retraction mechanism. The example device 1000 shown in FIG. 10 includes a housing 402 and a hypodermic needle assembly 1002. The hypodermic needle assembly 1002 and the housing 402 can include male and female lure interfaces that are used to couple the hypodermic needle assembly 1002 to the housing 402. Alternatively, the hypodermic needle assembly 1002 and the housing 402 can include threads that are used to couple the hypodermic needle assembly 1002 to the housing 402.

The hypodermic needle assembly 1002 includes a hypodermic needle 102. The hypodermic needle 102 includes a tube that can contain a volume of a substance. In one example, the hypodermic needle 102 is preloaded with a volume of a substance to discharge into a patient before the hypodermic needle assembly 1002 is coupled to the housing 402. In another example, the hypodermic needle 102 is preloaded with a volume of a substance to discharge into a patient before the hypodermic needle assembly 1002 is shipped to an operator. In various embodiments, the hypodermic needle 102 of hypodermic needle assemblies 1002 can be preloaded with various volumes of substances and color coded to indicate the volume of substance that is preloaded in the hypodermic needle 102.

The hypodermic needle assembly 1002 includes a spring 1004 that can form in part of a needle retraction mechanism. The spring 1004 is wrapped around the hypodermic needle 102 and engages a flange 1006 that extends out from the hypodermic needle 102. In engaging the flange 1006, the spring 1004 can apply a force to the hypodermic needle 102 to cause the hypodermic needle to retract back into the hypodermic needle assembly 1002.

Figure 11A:
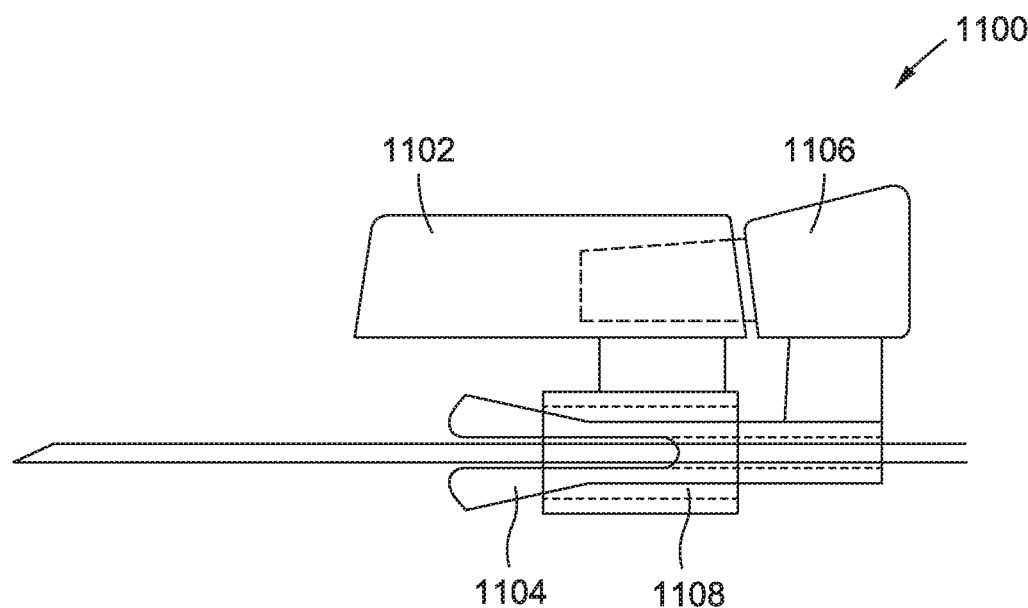
FIG. 11A depicts a cross-sectional view of an example of a holding assembly.

FIG. 11A depicts a cross-sectional view of an example of a holding assembly 1100. The example holding assembly 1100 shown in FIG. 11A can be used as part of a needle retraction mechanism, a rod displacement mechanism, a rod locking mechanism, or a needle locking mechanism. The example holding assembly 1100 includes a first piece 1102 that includes a collet 1104. The collet 1100 has an opening through which a needle or a rod that is threaded. The example holding assembly includes a second piece 1106 with a collet tightening mechanism 1108. The collet tightening mechanism 1108 is an opening that receives the collet 1104 and tightens the collet 1104 as the collet is moved into the collet tightening mechanism 1108. As a result, of tightening the collet 1104 the needle or rod that is threaded through the collet 1104 becomes secured to the first piece 1102 of the example holding assembly, such that as the first piece 1102 and the second piece 1106 are moved, the secured needle or rod moves with the first piece 1102 and the second piece 1106. As such, by securing a needle or a rod to the example holding assembly, the example holding assembly can be used to displace or retract the needle or the rod. Further, in securing a needle or a rod to the example holding assembly, the example holding assembly can be used to stop displacement of the needle or rod and lock the needle or rod into a specific position.

Figure 11B:
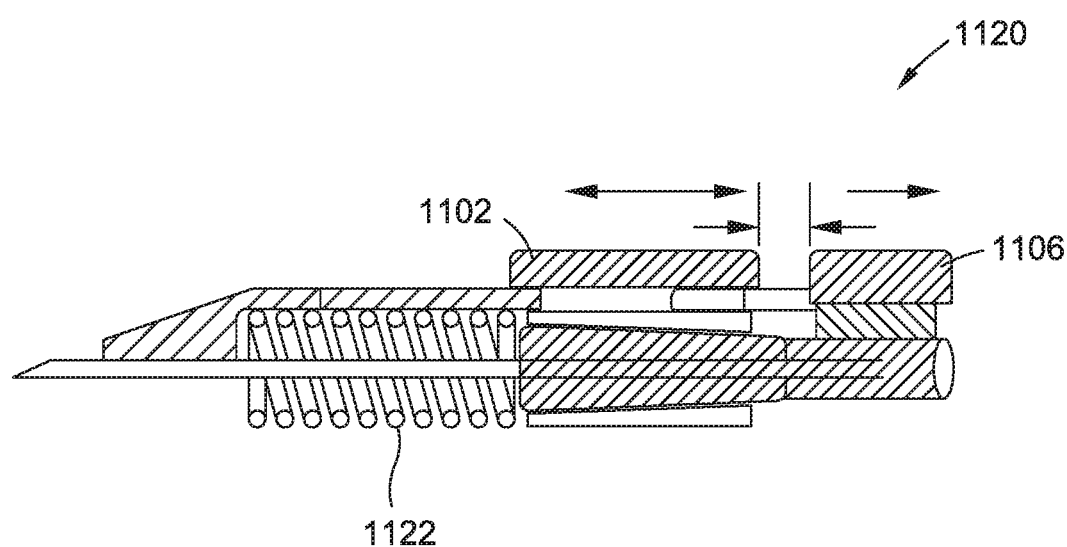
FIG. 11B depicts a cross-sectional view of an example of another holding assembly.

FIG. 11B depicts a cross-sectional view 1120 of an example of another holding assembly. The example holding assembly shown in FIG. 11B includes the same elements as the example holding assembly shown in FIG. 11A. Additionally, the example holding assembly shown in FIG. 11B includes a spring 1122 that is used to apply a force to the first piece 1102 to cause the first piece 1102 to displace towards the second piece 1106.

Figure 12:
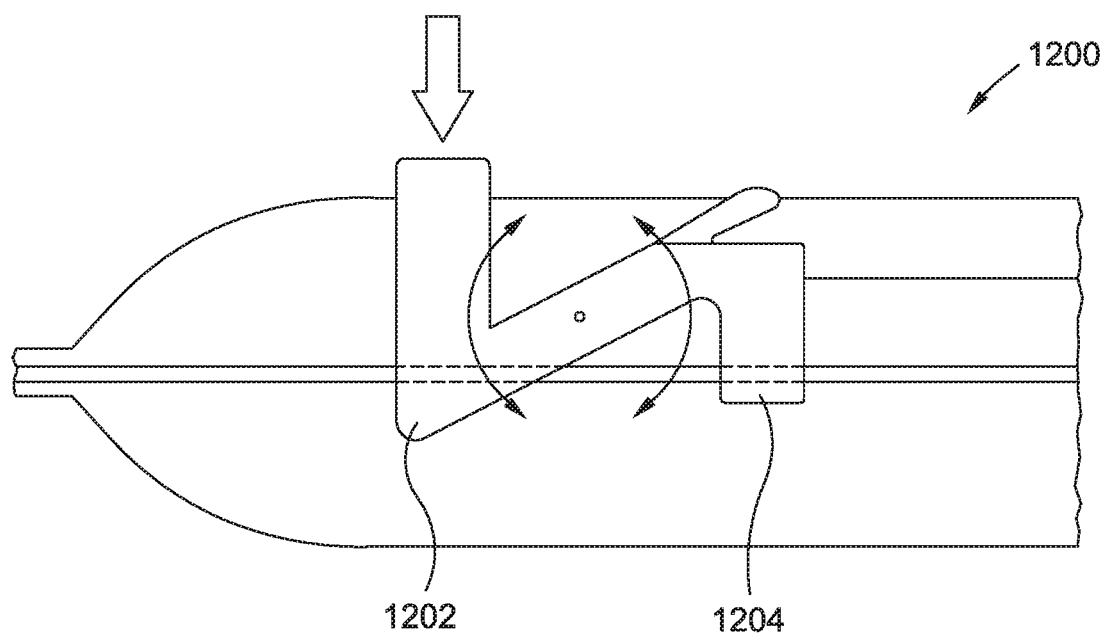
FIG. 12 depicts a side perspective view of an example of a portion selection assembly.

FIG. 12 depicts a side perspective view of an example of a portion selection assembly 1200. The portion selection assembly 1200 can be used with the various substance delivery devices described in this paper. The portion selection assembly 1200 can be used to select a portion of a volume of substance to discharge into a patient. The portion selection assembly 1200 includes a first region 1202 through which a volume of substance is threaded through and a second region 1204 through which the volume of substance is threaded through. In operation, an operator can slide the portion selection assembly 1200 such that either the first region 1202 or the second region 1204 is at the desired portion of the volume of substance to discharge into a patient. Further in operation, an operator can apply a force to the portion selection assembly 1200 to cause the selection assembly 1200 to rotate. In one example, as a result of rotating, the portion of the volume of substance is segmented in either or both the first region 1202 and the second region 1204. In another example, as a result of rotating, the portion of the volume of substance is secured against the portion selection assembly 1200 in either or both the first region 1202 and the second region 1204.

Figure 13:
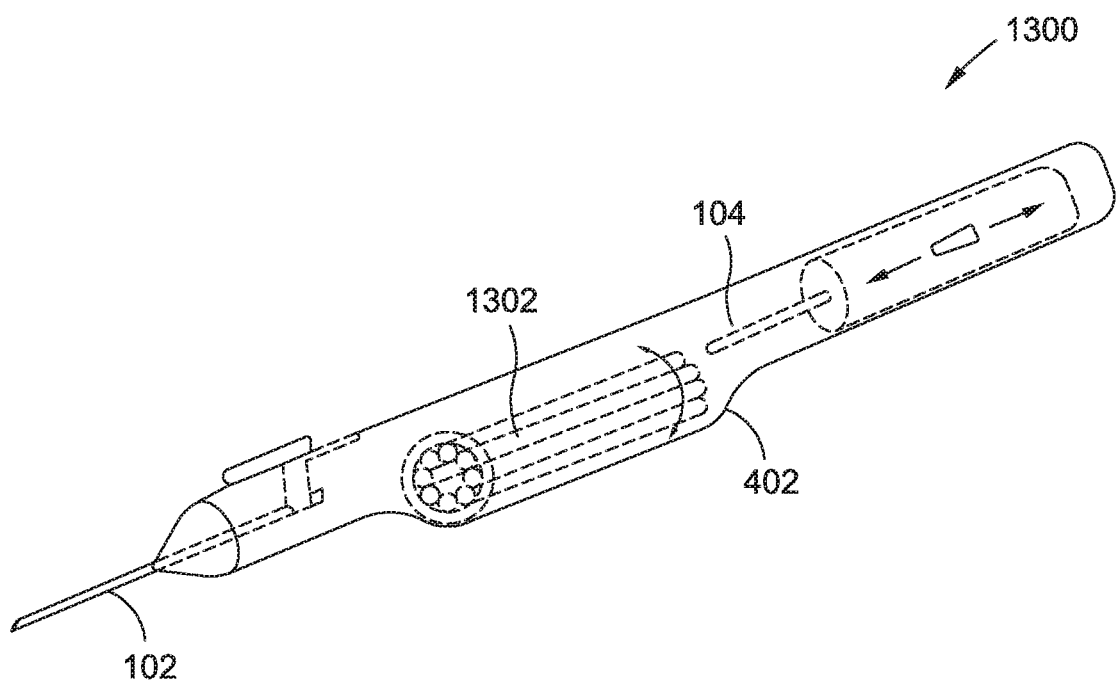
FIG. 13 depicts a cross-sectional perspective view of an example of a substance delivery device that includes a cartridge that holds multiple volumes of substances.

FIG. 13 depicts a cross-sectional perspective view of an example of a substance delivery device 1300 that includes a cartridge that holds multiple volumes of substances. The example substance delivery device 1300 shown in FIG. 13 includes a housing 402 coupled to a hypodermic needle 102. The housing 402 contains a rod 104 that can be displaced within the housing 402 and a tube within the hypodermic needle 102.

The housing 402 includes a substance cartridge 1302. The substance cartridge 1302 can be any mechanism that holds multiple volumes of substances. In one example the substance cartridge 1302 is a dermal thread cartridge that holds multiple dermal filler threads. The substance cartridge 1302 can hold various types of difference substances at the same time. The substance cartridge 1302 can be a revolving magazine that contains multiple chambers that can hold volumes of substances. The substance cartridge 1302 can be coupled to a substance cartridge positioning mechanism. In one example a substance cartridge positioning mechanism is a dermal thread cartridge positioning mechanism. The substance cartridge 1302 positioning mechanism can be any mechanism that allows an operator to position the substance cartridge 1302 such that a desired volume of substance can be pushed into the tube within the hypodermic needle 102 using the rod 104. In one example in which the substance cartridge 1302 is a revolving magazine, the substance cartridge positioning mechanism allows a user to revolve the revolving magazine until the chamber that contains the desires volume of substance is in the path in which the rod 104 is displaced within the housing 402.

Figure 14:
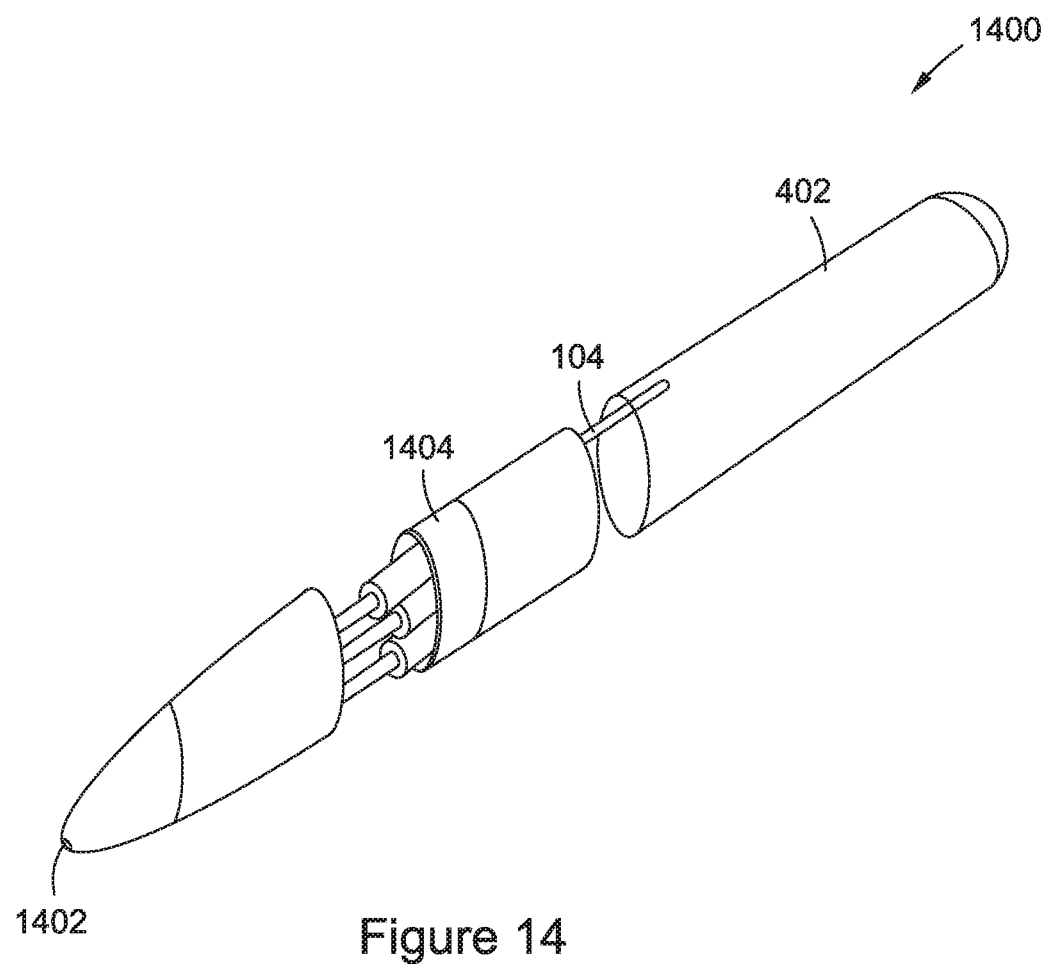
FIG. 14 depicts an exploded perspective view of an example of a substance delivery device that includes a needle cartridge that holds multiple needles.

FIG. 14 depicts an exploded perspective view of an example of a substance delivery device 1400 that includes a needle cartridge that holds multiple needles. The example substance delivery device shown in FIG. 14 includes a housing 402. The housing 402 includes an aperture 1402 through which needles can be extended out from and retracted back into the housing 402. The housing 402 contains a needle cartridge 1404 that contains a plurality of hypodermic needles. The hypodermic needles can be pre-loaded with a volume of a substance before the needle cartridge 1404 is loaded into the housing 402. In one example the needle cartridge 1404 is a revolving magazine that can be rotated to select a specific needle contained within the needle cartridge 1404.

The housing 402 contains a rod 104 that can be displaced within the housing. In being displaced within the housing 402, the rod 1408 can contact and apply a force to a needle in the needle cartridge 1404 thereby causing the needle to displace and extend out from the housing 402 through the aperture 1402. The rod 104 can include an outer cylinder region that is of a size greater than an inner tube of a hypodermic needle. As a result, the rod can engage the needle and apply a force against the needle to cause the needle to displace. Further in being displaced within the housing 402, the rod 104 can contact and apply a force to a volume of substance preloaded within a hypodermic needle to cause the substance to be discharged into a patient. The rod 102 can include an inner cylinder region that is of a size to fit within a tube of the hypodermic needle, thereby contacting and applying a force to a volume of substance contained within a tube of the hypodermic needle.

The needle cartridge 1404 can be coupled to a needle selection mechanism that allows an operator to select which needle to extend out from the housing 402. In an example where the needle cartridge is a revolving magazine, the needle selection mechanism can allow an operator to rotate the magazine such that the desired needle is in the path in which the rod 104 is displaced within the housing 402.

Compositions/Substances

As is used in this paper, dermal filler is a substance that is used to fill a wrinkle, a scar or a mark on a patient. Specifically, a dermal filler can be a substance that expands by absorbing fluids, thereby pushing out a wrinkle, a scar, or a mark, when deposited into a patient underneath the wrinkle, scar, or mark. A dermal filler can be a gel solution, including gel solutions that comprise hyaluronic acid, such as Restylane® and Juvederm®. A substance contained within the tube 106 can also include a dermal filler thread. A dermal filler thread is a substance, that is in a solid form at least before being deposited into a patient, and expands by absorbing fluid, thereby pushing out a wrinkle, a scar, or a mark, when deposited into the patient underneath the wrinkle, scar, or mark. A dermal filler thread can include a sheath that protects the dermal filler thread before it is discharged into a patient. A dermal filler thread can be biocompatible and compressible. Biocompatible refers to the fact that a substance will not produce a toxic, injurious, or immunological response in living tissue.

For example, suitable biocompatible threads can comprise epoxies, polyesters, acrylics, nylons, silicones, polyanhydride, polyurethane, polycarbonate, poly(tetrafluoroethylene), polycaprolactone, polyethylene oxide, polyethylene glycol, poly(vinyl chloride), polylactic acid, polyglycolic acid, polypropylene oxide, poly(alkylene)glycol, polyoxyethylene, sebacic acid polymers, polyvinyl alcohol, 2-hydroxyethyl methacrylate polymers, polymethyl methacrylate, 1,3-bis(carboxyphenoxy)propane polymers, lipids, phosphatidylcholine, triglycerides, polyhydroxybutyrate, polyhydroxyvalerate, poly(ethylene oxide), poly ortho esters, poly (amino acids), polycyanoacrylates, polyphophazenes, polysulfone, polyamine, poly (amido amines), fibrin, graphite, flexible fluoropolymer, isobutyl-based polymers, isopropyl styrene polymers, vinyl pyrrolidone polymers, cellulose acetate dibutyrate polymers, silicone rubber, hyaluronic acid, collagen, chondroitin sulfate, cyclodextrin, alginate, chitosan, carboxy methyl chitosan, heparin, gellan gum, agarose, cellulose, poly (glycerol-sebacate) elastomer, poly(ethylene glycol)-sebacic acid, poly(sebacic acid-co-ricinoleic acid), guar gum, xanthan gum, and combinations and/or derivatives thereof.

In certain embodiments, dermal filler threads are comprised of a thread of hyaluronic acid or salts, hydrates or solvates thereof or a thread of cross linked hyaluronic acid or salts, hydrates or solvates thereof or a combination thereof. Suitable hyaluronic acid threads are known in the art (see, e.g., WO 2010/028025, WO 2011/109130 and WO 2011/109129).

In certain embodiments, dermal filler threads are comprised of cross-linked hyaluronic acid or salts, hydrates or solvates thereof cross linked with butanediol diglycidyl ether (BDDE), divinyl sulfone (DVS) or 1-ethyl-3-(3-dimethylaminopropyl) carbodiimide hydrochloride (EDC). Those of skill in the art will appreciate that many other cross-linking agents may be used to cross-link hyaluronic acid or salts, hydrates or solvates thereof. The above list of cross-linking agents is illustrative rather than comprehensive. In one embodiment, the needle as disclosed herein is attached to a thread comprised of cross-linked hyaluronic acid or salts, hydrates or solvates thereof, wherein the hyaluronic acid has been cross linked with butanediol diglycidyl ether (BDDE).

In some embodiments, dermal filler threads are comprised of a thread of cross-linked hyaluronic acid. For example, in one embodiment, the cross-linked hyaluronic acid is a gel composition comprising at least 5% hyaluronic acid, wherein the hyaluronic acid is substantially cross-linked with at least about 15 mole % of a butanediol diglycidyl ether (BDDE) derivative relative to the repeating disaccharide unit of the hyaluronic acid. In some embodiments, the cross-linked hyaluronic acid further comprises a binder, such as noncross-linked hyaluronic acid.

In some embodiments, dermal filler threads that include cross-linked hyaluronic acid can be prepared using a composition comprising substantially cross-linked hyaluronic acid, wherein hyaluronic acid is cross-linked with at least about 15 mole % of a butanediol diglycidyl ether (BDDE) derivative relative to the repeating disaccharide unit of the hyaluronic acid. In some embodiments, the composition comprises at least 5% hyaluronic acid before cross-linking, such as 8%, 10% or 12% hyaluronic acid. Further, in some embodiments, the threads include both cross-linked and noncross-linked hyaluronic acid.

Various aspects of the thread manufacturing process (e.g., rinsing, deaeration, extrusion, and drying of precursor gels, as well as the terminal sterilization of the dry threads) can be altered to produce threads having improved physical characteristics, suitable for the present technology. Specifically, threads comprising cross-linked hyaluronic acid can be prepared with significant cross-linking (e.g., at least about 15% BDDE derivative) relative to the repeating disaccharide unit of the hyaluronic acid. Further information about compositions and methods for preparing threads suitable for use in the present technology can be found at United States Patent Publication 2013-0122068, WO 2010/028025; WO 2011/109129; WO 2011/109130; WO 2012/054301; WO 2012/054311; the content of which is incorporated into the present disclosure by reference in its entirety.

Also contemplated for use with the device described herein are one or more alternative shapes, including spheres, cylinders, oval, etc. For example, a plurality of spheres may be delivered to the desired location. Spherical forms useful in the devices described herein are more fully described in U.S. patent application Ser. No. 14/604,017, filed on Jan. 23, 2015, entitled "Spherical Forms of Cross-Linked Hyaluronic Acid and Methods of Use Thereof", the entire disclosure of which is incorporated herein by this specific reference.

In one embodiment, the threads or spheres are comprised of hyaluronic acid or a salt thereof, wherein the hyaluronic acid is cross-linked in with butane diglycidyl ether (BDDE). In another embodiment, the threads or spheres further comprise noncross-linked hyaluronic acid or a salt thereof.

We claim:

1. A device for implanting a substance into subcutaneous tissue or the dermis of a patient, the device comprising:
    a housing;
    a needle cartridge contained in the housing and including a hypodermic needle;
    the hypodermic needle including a tube preloaded with a dermal filler thread and an aperture on a distal end of the hypodermic needle forming an opening of the tube on the distal end of the hypodermic needle; and
    a rod comprising an outer cylinder and an inner cylinder, the outer cylinder being of a size larger than a diameter of the tube and configured to extend the hypodermic needle through a housing aperture of the housing, the outer cylinder including a hollow region extending through a length thereof, and the inner cylinder movable in the hollow region of the outer cylinder, the inner cylinder being of a size smaller than the diameter of the tube and configured to extend beyond the outer cylinder to fit within the tube and apply a force to the dermal filler thread preloaded in the hypodermic needle.

2. The device of claim 1 further comprising a rod locking mechanism configured to engage the rod.

3. The device of claim 1 further comprising a rod displacement mechanism configured to apply a force to the rod.

4. The device of claim 3 wherein the rod displacement mechanism is a twist-feed mechanism.

5. The device of claim 3, wherein the rod displacement mechanism is a spring-loaded mechanism.

6. The device of claim 1 wherein the dermal filler thread is a hyaluronic acid thread.

7. The device of claim 1 wherein the dermal filler thread is a crosslinked hyaluronic acid thread.

8. A method of reducing appearance of a wrinkle in the skin of a patient, the method comprising:
    utilizing a device to deliver a dermal filler thread beneath said wrinkle, wherein the device comprises
    a hypodermic needle including a tube preloaded with the dermal filler thread and an opening on a distal end of the hypodermic needle, and
    a rod comprising an outer cylinder and an inner cylinder, the outer cylinder being of a size larger than a diameter of the tube and configured to extend to the hypodermic needle through a device aperture of the device, the outer cylinder including a hollow region extending through a length thereof, and
    the inner cylinder movable in the hollow region of the outer cylinder, the inner cylinder being of a size smaller than the diameter of the tube and configured to extend beyond the outer cylinder to fit within the tube and apply a force to the dermal filler thread to force the dermal filler out of the tube and into the skin when the hypodermic needle is placed in the skin.

9. The method of claim 8 wherein the dermal filler thread is a hyaluronic acid thread.

10. The method of claim 8 wherein the dermal filler thread is a crosslinked hyaluronic acid thread.

\* \* \* \* \*